United States Patent [19]

Walker

[11] 4,039,677

[45] Aug. 2, 1977

[54] NOVEL 1-PHENETHYLIMIDAZOLES

[75] Inventor: Keith A. M. Walker, Palo Alto, Calif.

[73] Assignee: Syntex (U.S.A.) Inc., Palo Alto, Calif.

[21] Appl. No.: 662,784

[22] Filed: Mar. 1, 1976

[51] Int. Cl.$^2$ .................. A61K 31/415; C07D 233/60
[52] U.S. Cl. .................................... 424/273; 542/427; 548/341
[58] Field of Search ................ 260/309, 240 D, 240 J; 424/273

[56] References Cited

U.S. PATENT DOCUMENTS

| 3,658,813 | 4/1972 | Godefroi et al. | 260/309 |
| 3,717,655 | 2/1973 | Godefroi et al. | 260/309 |
| 3,749,701 | 7/1973 | Engelhard et al. | 260/309 |
| 3,892,764 | 7/1975 | Metzger et al. | 260/309 |

Primary Examiner—Natalie Trousof
Attorney, Agent, or Firm—Tom M. Moran; William B. Walker

[57] ABSTRACT

Novel 1-phenethylimidazoles substituted at the position $\beta$ to the imidazole ring by an optionally substituted hydrocarbyl carbonate or a mono-, di-, or trithiocarbonate are useful as antimicrobial agents and as intermediates in the preparation of novel 1-phenethylimidazoles substituted at the position $\beta$ to the imidazole with a mercapto. Both the former and latter compounds are useful as intermediates in the preparation of certain 1-[$\beta$-(R-thio)phenethyl]imidazoles.

37 Claims, No Drawings

NOVEL 1-PHENETHYLIMIDAZOLES

BACKGROUND OF THE INVENTION

1. Field of the Invention

This invention relates to novel 1-phenethylimidazoles substituted at the position β to the imidazole ring by an optionally substituted hydrocarbyl carbonate or a mono-, di-, or trithiocarbonate, the use of these imidazoles as antimicrobial agents, the combination of these imidazoles with a suitable carrier, the preparation of these imidazoles, and the use of these imidazoles as intermediates in the preparation of 1-[β-(R-thio)phenethyl]imidazoles.

This invention further relates to certain novel 1-phenethylimidazoles substituted at the position β to the imidazole ring with a mercapto and the acid and base salts thereof, the preparation of these imidazoles, and the use of these imidazoles in the preparation of 1-[β-(R-thio)phenethyl]imidazoles as well as other 1-phenethylimidazoles substituted at the position β to the imidazole ring with a mono-, di- or trithiocarbonate or a thio-or dithioester.

2. Prior Art

It is generally known in the art that certain 1-(β-aryl)-ethylimidazole ethers and amines have anti-fungal and anti-bacterial activity. See, for example, U.S. Pat. Nos. 3,717,655 and 3,839,574, both to Godefroi and Herres of Janssen and U.S. Pat. No. 3,658,813 to Godefroi and Schuermans of Janssen. Representative of the ethers is the compound miconazole nitrate having the formula

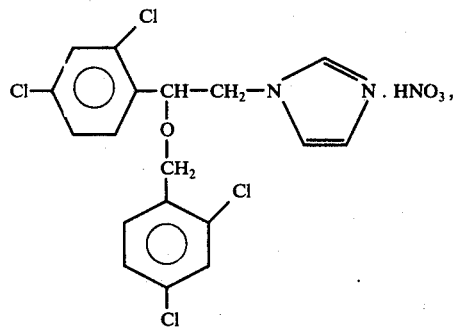

the active ingredient in Monistat® Cream sold by Ortho Pharmaceutical Co. Such compounds are derived from 1-(β-hydroxyphenethyl)imidazole or 1-(β-aminophenethyl)-imidazoles which are optionally substituted on the phenyl ring. (See Godefroi, et al, *J. Med. Chem.*, 12, 784–91 (1969). Other 1-ethylimidazoles which are known include those disclosed in U.S. Pat. Nos. 3,796,704 and 3,892,764 both to Metzger et al. of Bayer and U.S. Pat. No. 3,914,427 to Kramer et al. of Bayer. These, too, show anti-fungal activity.

An entirely new class of 1-(β-substituted phenethyl)-imidazoles has now been discovered which shows very good anti-fungal and anti-bacterial activity. These are the 1-phenethylimidazoles which are substituted at the position β to the imidazole with a carbonate or a mono-, di-, or trithiocarbonate. The existence of related compounds was hinted in the broad disclosure U.S. Pat. No. 3,796,704 but, unfortunately, no method was given for preparing such compounds.

SUMMARY OF THE INVENTION

The first aspect of the present invention relates to novel imidazole derivatives and more particularly to 1-phenethylimidazoles having the formula:

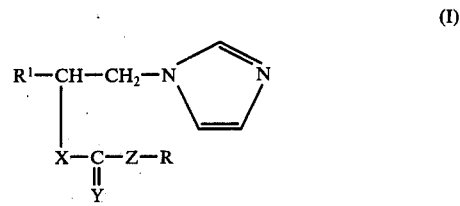

(I)

and the antimicrobial acid addition salts thereof, wherein

R is alkyl, phenylalkenyl, substituted phenylalkenyl, cycloalkyl, cycloalkyl lower alkyl, phenylalkyl, substituted phenylalkyl, phenyl and substituted phenyl, said substituted phenyl, substituted phenylalkenyl, and substituted phenylalkyl containing at least one substitutent on the phenyl moiety selected from the group consisting of halo, lower alkyl and trifluoromethyl;

$R^1$ is phenyl optionally substituted with one or more substituents chosen from the group consisting of halo, lower alkyl and trifluoromethyl; and X, Y and Z are independently sulfur or oxygen. The subject compounds of Formula (I), above, exhibit antifungal, antiprotozoal and antibacterial activity against animal and human pathogens as well as antifungal activity against fungi of primarily agricultural importance. Thus, the subject compounds are found to be useful antimicrobials, having not only pharmaceutical but also agricultural and industrial applications. Thus, a further aspect of the present invention relates to methods of inhibiting the growth of fungi, protozoa, and bacteria by applying to a host object containing, or subject to attack by, fungi, protozoa or bacteria, a fungicidally, protozoicidally, or bactericidally effective amount of a compound of this invention. A still further aspect of the present invention relates to compositions for pharmaceutical, agricultural, and industrial use, which compositions comprise the subject compounds of Formula (I) in combination with a suitable carrier.

Still another aspect of the present invention is the preparation of the compounds of Formula (I) set forth above. This will be discussed hereinafter more completely.

Still another aspect of this invention relates to the use of the compounds of this invention in preparing 1-[β-(R-thio)phenethyl]imidazoles.

Finally, another aspect of this invention is a compound chosen from those represented by

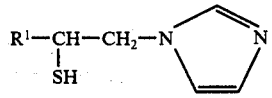

(II)

wherein $R^1$ is defined hereinbefore, especially 2,4-dichlorophenyl, and the acid or base salts thereof. A salt of the compound of formula (II) may be prepared by reacting a compound of Formula (I) where X is S with a suitable base. By reacting a compound of Formula (II) with R²B or 

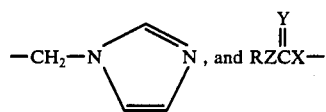

wherein R, Y and Z are previously defined, A and B are suitable leaving groups, and R² is defined hereinafter, the compounds of Formula (I), 1-[β-(R²-thio)phenethyl]imidazoles, or the compounds of U.S. patent application Ser. No. 662,786 filed Mar. 1, 1976, may be respectively obtained.

Specific representative embodiments of the compounds, compositions, uses of and processes for preparing compounds of this invention will be discussed more completely and specifically hereinafter.

PREFERRED EMBODIMENTS

Compounds of the Invention

A. Definitions

The term "alkyl" as used in the specification and appended claims refers to a saturated, unbranched or branched acyclic hydrocarbon group containing 1 to 12 carbon atoms inclusive, such as methyl, ethyl, n-propyl, isopropyl, n-butyl, i-butyl, t-butyl, n-pentyl, n-heptyl, n-octyl, n-nonyl, n-dodecyl and the like. The term "lower alkyl" refers to an alkyl group as previously defined containing 1 to 4 carbon atoms, inclusive.

The term "cycloalkyl" as used herein refers to a saturated, monocyclic hydrocarbon group having 5–8 ring carbon atoms, e.g. cyclohexyl. The term "cycloalkyl lower alkyl" refers to a cycloalkyl group as previously defined attached to an unbranched acyclic hydrocarbon group containing 1 to 4 carbon atoms, such as cyclopentylpropyl, cyclohexylmethyl, cyclooctylethyl, and the like. The term "phenylalkenyl" refers to a hydrocarbon moiety in which the alkenyl portion containing 3 to 4 carbon atoms is attached to a phenyl ring such as 3-phenyl-2-propenyl, 4-phenyl-3-butenyl, and the like. The term "phenylalkyl" refers to a hydrocarbon moiety in which the alkyl portion contains 1 to 3 carbon atoms. Representative examples include benzyl, 3-phenylpropyl and the like. The term "halo" as used herein refers to chloro, fluoro and bromo. The term "antimicrobial acid addition salts" refers to salts of the subject compounds which possess the desired activity and which exhibit minimal undesirable biological or other effects. These salts are formed by reacting a compound represented by formula (I) with inorganic acids such as hydrochloric acid, hydrobromic acid, sulfuric acid, nitric acid and phosphoric acid and the like, or organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

All compounds of Formula (I) [and Formula (II)] have at least one chiral center, i.e., the carbon atom to which are attached the R¹, H—, [or —SH in Formula (II)] moieties. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form, but to encompass the individual optical isomers of the subject compounds.

If desired, racemic intermediates or final products prepared herein may be resolved into their optical antipodes by conventional resolution means known per se, for example, by the separation (e.g. fractional crystallization) of the diastereomeric salts formed by reaction of, e.g. racemic compounds of Formula (I) or the racemic alcohol precursors of Formula (III), infra, with an optically active acid, or of the diastereomeric esters formed by reaction of the racemic compounds of Formula (II) or the racemic alcohol precursors of Formula (III) with an optically active acid. Exemplary of such optically active acids are the optically active forms of camphor-10-sulfonic acid, α-bromocamphor-π-sulfonic acid, camphoric acid, menthoxyacetic acid, tartaric acid, malic acid, diacetyltartaric acid, pyrrolidone-5-carboxylic acid, and the like. The separated pure diastereomeric salts or esters may then be cleaved by standard means to afford the respective optical isomers of the compounds of Formulae (I) or (II) of the precursor alcohols of Formula (III). Particularly valuable is the resolution of an alcohol of Formula (III), e.g. by fractional crystallization of a salt with an optically active acid (e.g. dibenzoyl tartarate). The thus resolved alcohol may then be employed as discussed hereinafter to prepare the compounds of this invention.

B. Specific Sub-Groups of Formula (I)

Eminently suitable as the compounds of this invention represented by Formula (I) are those wherein R is as follows:

alkyl of up to 10 carbons such as methyl, ethyl, propyl, isopropyl, n-butyl, isobutyl, t-butyl, n-pentyl, n-hexyl, n-heptyl, n-octyl, n-nonyl, n-decyl and the like, alkyls of 1 to 4 carbon atoms, both branched or straight chain, and those of 5 to 10 straight chain carbon atoms being preferred;

phenyl optionally substituted with one or more (preferably 1 or 2) substituents chosen from halo or lower alkyl, when only one substituent is present it is preferably at the 4-position, particularly 4-chloro, 4-bromo, 4-fluoro, and when two substituents are present they are preferably halo at the 2,4- or 3,4-positions, chloro being the most particularly preferred substituent in either case;

benzyl optionally substituted on the phenyl ring with one or more (preferably 1 or 2) substituents chosen from halo or lower alkyl, when only one substituent is present, it is preferably halo at the 4-position and when two substituents are present they are preferably halo at the 2,4- or 3,4-positions, chloro being the most particularly preferred substituent in either case; or 3-phenyl-2-propenyl optionally substituted at the 4-position of the phenyl ring with a halo, preferably chloro.

Eminently suitable as the compounds of Formula (I) are those wherein $R^1$ is phenyl substituted with 1 to 3 substituents chosen from halo and lower alkyl, preferably 4-halophenyl, (particularly 4-chlorophenyl) 2,4- or 3,4-dihalophenyl (particularly 2,4-dichlorophenyl), or 2,4,6-trichlorophenyl.

Especially suitable as combinations of X, Y and Z are those wherein at least one of the components is S, particularly the following combinations:

$$-S-\underset{O}{\overset{\parallel}{C}}-O-R, \quad -S-\underset{S}{\overset{\parallel}{C}}-S-R, \quad -S-\underset{O}{\overset{\parallel}{C}}-S-R,$$

$$-O-\underset{O}{\overset{\parallel}{C}}-S-R, \quad \text{and} \quad -S-\underset{S}{\overset{\parallel}{C}}-O-R,$$

preferably X is S. The xanthate $$(-S-\underset{S}{\overset{\parallel}{C}}-O-R)$$

is particularly preferred.

In the case where $R^1$ is 2,4-dichlorophenyl or 4-chlorophenyl and (a) where X, Y and Z are each oxygen (O), then R, if an alkyl, will preferably contain 4–9 carbon atoms; (b) where one of X, Y or Z is sulfur (S) and the other two are O, then R, if an alkyl, will preferably have 2–7 carbon atoms; (c) where one of X, Y, or Z is O and the other 2 are S, then R, if alkyl, will preferably contain 1–7 carbon atoms; and (d) where all of X, Y and Z are S, then R, if alkyl, will preferably have 1–5 carbon atoms.

An extremely preferred subclass of the compounds of this invention are those encompassed by the formula of I, above, wherein
- $R^1$ is 2,4-dichlorophenyl,
- R is alkyl of 1–7 carbon atoms, phenyl substituted with halo, particularly chloro, at 1 to 2 positions, (especially 4-chloro, 3,4-dichloro or 2,4-dichloro), benzyl substituted at the 4-position (i.e., p-substituted) with a halo (especially chloro) or at the 2,4- or 3,4- positions with chloro;
- X is S; and
- Y and Z are independently S or O.

C. Specific Sub-Groups of Formula (II)

Particularly valuable compounds of this invention represented by Formula (II) are those wherein $R^1$ is phenyl having 1 to 3 substituents chosen from halo and lower alkyl, preferably 4-halophenyl (particularly 4-chlorophenyl), 2,4- or 3,4-dihalophenyl (particularly 2,4-dichlorophenyl), or 2,4,6-trichlorophenyl and the acid or base addition salts thereof. Particularly preferred is the compound of Formula (II) wherein $R^1$ is 2,4-dichlorophenyl, namely 1-[2,4-dichloro-β-(mercapto)phenethyl]imidazole and its acid or base addition salts.

Specific examples of each of these sub-groups of part B and C, above, may be found in the examples contained in the specification hereinafter.

In naming the compounds of this invention represented by Formula (I), the following nomenclature is used for the combinations of X, Y and Z (assuming $R^1$ is 2,4-dichlorophenyl and R is ethyl):

1. When X, Y and Z are all O, the compound is 1-[2,4-dichloro-β-(ethoxycarbonyloxy)phenethyl]imidazole;
2. When X is S and Y and Z are O, the compound is 1-[2,4-dichloro-β-(ethoxycarbonylthio)phenethyl]imidazole;
3. When Y is S and X and Z are O, the compound is 1-[2,4-dichloro-β-(ethoxythiocarbonyloxy)phenethyl]imidazole;
4. When Z is S and X and Y are O, the compound is 1-[2,4-dichloro-β-(ethylthiolcarbonyloxy)phenethyl]imidazole;
5. When X is O and Y and Z are S, the compound is 1-[2,4-dichloro-β-(ethylthiolthiocarbonyloxy)phenethyl]imidazole.
6. When Y is O and X and Z are S, the compound is 1-[2,4-dichloro-β-(ethylthiolcarbonylthio)phenethyl]imidazole;
7. When Z is O and X and Y are S, the compound is 1-[2,4-dichloro-β-(ethoxythiocarbonylthio)phenethyl]imidazole; and
8. When X, Y and Z are all S, the compound is 1-[2,4-dichloro-β-(ethylthiolthiocarbonylthio)phenethyl]imidazole.

In naming the compounds of Formula (II) if $R^1$ is 2,4-dichlorophenyl, the compound is named 1-[2,4-dichloro-β-(mercapto)-phenethyl]imidazole.

Utility, Formulation and Administration

The subject compounds of Formula (I) exhibit anti-fungal and anti-bacterial activity. For example, compounds of the present invention exhibit anti-fungal activity against human and animal pathogens such as

| | |
|---|---|
| Microsporum audouini, | Trichophyton rubrum, |
| Microsporum gypseum, | Trichophyton tonsurans, |
| Microsporum gypseum-canis, | Candida albicans, |
| Epidermophyton floccosum, | Cryptococcus neoformans, and |
| | Trichophyton mentagrophytes |

Compounds of the present invention represented by Formula (I) also exhibit antifungal activity against fungi of primarily agricultural importance such as

| | |
|---|---|
| Aspergillus flavus, | Aspergillus niger, |
| Cladosporium herbarum, | Penicillium oxalicum, |
| Fusarium graminearum, | Penicillium spinulosum, and |
| Penicillium notatum, | Pithomyces chartarum. |

In addition, the compounds of the present invention represented by Formula (I) exhibit anti-bacterial activity against human and animal pathogens, such as

| | |
|---|---|
| Staphylococcus aureus, | Proteus vulgaris, |
| Streptococcus faecalis, | Salmonella choleraesuis, |
| Corynebacterium acnes, | Pasteurella multocida, and |
| Erysipelothrix insidiosa, | Pseudomonas aeruginosa. |
| Escherichia coli, | |

Furthermore, compounds represented by Formula (I) exhibit anti-protozoal activity against certain human pathogens such as *Trichomonas vaginalis*.

In view of the aforementioned activities, the subject compounds are found to be useful antimicrobials, having not only pharmaceutical but also agricultural and industrial application.

Accordingly, a further aspect of the present invention relates to compositions for pharmaceutical, agricultural, and industrial use, which compositions comprise the subject compounds of Formula (I) in combination with a suitable carrier. A still further aspect of the present invention relates to methods of inhibiting the growth of fungi and bacteria by applying to a host object containing, or subject to attack by, fungi, protozoa, or bacteria, a fungicidally, protozoicidally, or bacteriocidally effective amount of a compound of Formula (I) or a suitable composition containing same.

In pharmaceutical formulations compositions may be solid, semi-solid or liquid in form such as tablets, capsules, powders, suppositories, liquid solutions, suspensions, creams, lotions, gels, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semi-solid formulations there may be mentioned, for example, polyalkylene glycols, vaseline, petrolatum and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials.

The pharmaceutical compositions of this invention typically comprise a pharmaceutically acceptable, non-toxic carrier in combination with one or more compounds represented by Formula (I) in an amount effective for relief or prevention of the specific condition being treated. Since the active compounds of this invention exhibit anti-fungal, anti-bacterial and anti-protozoal activity over a wide range of concentration, the effective amount may vary. For example, in topical formulations the amount may be about 0.1% by weight (%w) to about 10%w of the total pharmaceutical formulation while in other formulations the amount may be about 5 to 95%w or more. Preferably the pharmaceutical compositions of this invention are formulated in unit dosage form to facilitate administration (unit dosage being the amount of active ingredients administered on one occasion).

In pharmaceutical applications, the subject compounds and compositions may be administered to humans and animals by conventional methods, e.g. topically, orally, parenterally and the like. "Topical" administration includes intravaginal application while parenteral administration includes intramuscular as well as subcutaneous and intravenous injection. Intravenous injection of imidazole derivatives for certain systemic conditions has been demonstrated to be effective (see for example, *Drugs* 9, 419–420 (1975), which describes the intravenous administration of Miconazole, i.e. 1-[2,4-dichloro-$\beta$-(2',4'-dichlorobenzyloxy)phenethyl]imidazole nitrate, to patients with systemic candidiasis). Topical application is the preferred method of administration in pharmaceutical applications. For such treatment, an area having an existing fungal, protozoal or bacterial growth, or to be protected against attack by fungi, protozoa, or bacteria, may be treated with the subject compounds of Formula (I) or compositions by, for example, dusting, sprinkling, spraying, rinsing, brushing, dipping, smearing, coating, impregnating and the like.

The exact regimen for pharmaceutical administration of the compounds and compositions disclosed herein will necessarily be dependent upon the needs of the individual subject being treated, the type of treatment, e.g., whether preventative or curative, the type or organism involved and, of course, the judgment of the attending practitioner. In general, for systemic (e.g., oral or parenteral) administration it is expedient to administer the active ingredient in amounts of between about 1 and 100 mg/kg body weight per day (preferably between about 5 and 50 mg/kg. body weight per day) preferably distributed over several applications (e.g., in 3 individual doses) in order to achieve effective results. For localized (e.g., topical) administration, however, proportionately less of the active ingredient is required.

In agricultural applications, the subject compounds may be applied directly to plants (e.g., seeds, foliage) or to soil. For example, compounds of the present invention may be applied to seeds alone or in admixture with a powdered solid carrier. Typical powdered carriers are the various mineral silicates, e.g., mica, talc, pyrophyllite, and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject compounds can be applied as a dust in admixture with sand, soil or a powdered solid carrier such as mineral silicate with or without additional surface-active agent, or the subject compounds can be applied as an aqueous spray optionally containing a surface-active dispersing agent and a powdered solid carrier. As a foliage treatment, the subject compounds may be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known manner. Materials capable of supporting bacteria and fungi may be protected by contacting, mixing or impregnating these materials with the subject compounds. In order to increase their effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

PROCESS FOR PREPARING COMPOUNDS OF THE INVENTION

Compounds of this invention represented by Forumula (I) may be prepared from several unique processes. For example these compounds may be prepared from (A) an alcohol or a suitable metal salt thereof, e.g., a 1-[$\beta$-hydroxyphenethyl]imidazole or its sodium salt, (B) a halide or reactive ester, e.g. a 1-($\beta$-halophenethyl)imidazole, or (C) from a mercaptan or a suitable metal salt thereof, i.e., a 1-($\beta$-mercaptophenethyl)-imidazole or its sodium salt.

A. When starting from an alcohol such as a 1-[substituted-$\beta$-hydroxy phenethyl]imidazole represented by Formula (III) or a suitable metal salt thereof, the alcohol (or salt) is reacted with a carbonyl chloride to give the desired product according to the equation set forth below

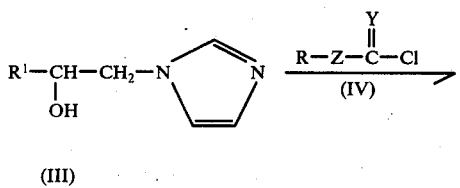

(III)

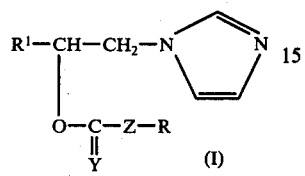

wherein $R^1$, R, Y and Z have the values set forth hereinbefore. Note that a suitable salt of the compound of Formula (III) such as an alkali or alkaline earth metal salt, e.g. sodium, potassium or lithium salt may also be used. Thus, by reacting an R-oxycarbonyl chloride (Y and Z both O in IV, above) with the appropriate 1-(β-hydroxyphenethyl)imidazole one obtains the corresponding 1-(β-R-oxycarbonyloxy)phenethyl]imidazole. Similarly from the R-thiolcarbonyl chloride (Z is S and Y is O) one obtains the 1-[β-(R-thiolcarbonyloxy)-phenethyl]imidazoles, from the R-dithiocarbonyl chloride (Y and Z are both S) one obtains the 1-[β-(R-thiolthiocarbonyloxy)phenethyl]imidazole, and from the R-oxythiocarbonyl chloride (Z is O and Y is S) one obtains the 1-[β-(R-oxythiocarbonyloxy)phenethyl]imidazole.

In carrying out the reaction of this process the 1-[β-hydroxyphenethyl]imidazole may be reacted directly with the carbonyl chloride in the presence of a base. Preferably when a thiocarbonyl chloride such as

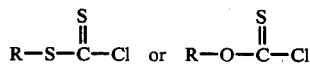

is reacted, the base salt of the alcohol is the co-reactant. In the case of the reaction of the imidazole directly with the carbonyl or thiocarbonyl chloride, a suitable solvent is used for dissolving or suspending the reactants and a base may be added to aid in the reaction. Suitable solvents include dichloromethane, chloroform, pyridine, tetrahydrofuran, benzene, toluene, acetone, hexamethylphosphoramide, dimethylformamide and the like while suitable bases include (when needed) triethylamine, pyridine, potassium carbonate, 4-dimethylaminopyridine, and the like.

Generally the temperature is about −20° to 80° C, preferably 0°-30° C and the reaction is carried out at atmospheric pressure. At least 1 mole of the carbonyl chloride is reacted with 1 mole of the starting compound (III) for complete reaction to take place. Preferably the mole ratio of the carbonyl or thiocarbonyl chloride to compound (III) is between about 1:1 to 2:1.

The starting compounds of Formula (III) may be prepared by a variety of reaction sequences, the most important of which will be discussed hereafter under "Preparations of Starting Materials".

In some instances it is preferable to first form a salt of the 1-[β-hydroxyphenethyl]imidazole, e.g., before reaction with a thiocarbonyl chloride. For example, the sodium salt may be prepared by reacting the alcohol of Formula (III) with sodium hydride in a suitable solvent such as hexamethylphosphoramide, dimethylformamide, tetrahydrofuran and the like at a temperature of about 0° to 100°, generally about 10° to 50° C. Other suitable salts may be prepared by reacting the appropriate hydride, that is an alkali metal hydride or alkaline earth metal hydride with the 1-[β-hydroxyphenethyl]imidazole. Examples of these bases include potassium hydride, lithium hydride, calcium hydride, and the like.

B. A method for preparing the compounds of this invention represented by Formula (I) where X is S and R is as previously defined (except optionally substituted phenyl) comprises reacting an appropriate compound of Formula (VI) with a suitable metal R-thiocarbonate, R-dithiocarbonate or R-trithiocarbonate salt. This reaction sequence can be depicted by the following equation:

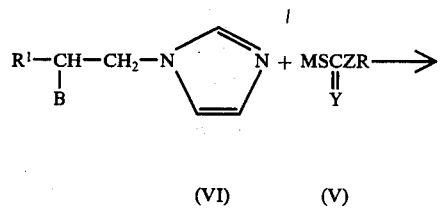

(VI)   (V)

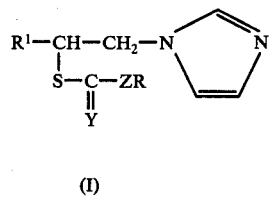

(I)

wherein M is a suitable metal such as an alkali metal, e.g., sodium, potassium or lithium, or an alkaline earth metal; B is a reactive leaving group such as a tosylate, mesylate or halo, preferably chloro; and $R^1$, Y and Z have the definitions presented hereinbefore. Thus by reacting a 1-[β-halophenethyl]imidazole with, for example, an appropriate potassium-O-R thiocarbonate there is obtained the corresponding 1-[β-(R-oxycarbonylthio) phenethyl]-imidazole, from potassium O-R dithiocarbonate is obtained the corresponding 1-[β-(R-oxythiocarbonylthio)phenethyl]imidazole, and from the potassium hydrocarbyl trithiocarbonate compound is obtained the corresponding 1-[β-(R-thiolthiocarbonylthio) phenethyl]-imidazole. In this series of reactions generally the reactants are placed in a suitable solvent such as an alcohol (e.g. methanol, ethanol) or acetone and are reacted at temperatures of from 0° to 70°, generally under atmospheric conditions. The reactants may be present at mole ratios of 1 to 3 moles of the carbonate per mole of the starting imidazole (VI). An acid salt of the imidazole of Formula (VI) may also be used if excess of the metal mono-, di-, or trithiocarbonate is employed. The starting imidazole depicted as Formula (VI) of this process may be prepared by methods known in the art such as those disclosed in U.S. Pat. No. 3,679,697 to Kreider and Twelt.

The R metal thiocarbonates may be prepared by methods disclosed in E. E. Reid, *Organic Chemistry of Bivalent Sulfur*, Vol. IV, Chemical Publishing Co., Inc., New York, New York (1962). As much of this disclosure as is pertinent is incorporated herein by reference.

C. Another process for making the compounds of Formula (I) wherein X is S involves reacting a compound of this invention of the Formula (II) or a suitable acid or base salt thereof with a suitable carbonyl or thiocarbonyl halide, preferably a carbonyl or thiocarbonyl chloride. A suitable base salt has a formula

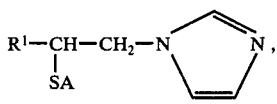

(IIa)

A is a suitable metal such as an alkaline earth or preferably alkali metal such as lithium, potassium, or especially sodium and $R^1$ is as previously defined. Thus, by reacting the mercaptide set forth in Formulae (II) or (IIa) above with at least one molar equipment of an R-oxycarbonyl chloride, the corresponding 1-[β-(R-oxycarbonylthio)phenethyl]imidazole is obtained. Similarly, from R-thiolcarbonyl chloride, R-dithiocarbonyl chloride, and an R-oxythiocarbonyl chloride the corresponding 1-[β-(R-thiolcarbonylthio)phenethyl]imidazole, 1-[β-(R-thiolthiocarbonylthio)phenethyl]imidazole and 1-[β-(R-oxythiocarbonylthio)phenethyl]imidazole are obtained respectively.

It is to be understood that the compounds represented by Formulae (II) and (IIa) may be prepared and reacted in situ or they may be first prepared and isolated then reacted with the appropriate carbonyl or thiocarbonyl chloride. In this process the compounds represented by Formula (IIa) are prepared from a compound of this invention represented by Formula (I) such as a 1-[β-(R-oxythiocarbonylthio)phenethyl]imidazole or its acid salt as exemplified by 1-[2,4-dichloro-β-(ethoxythiocarbonylthio)phenethyl]imidazole, by treating the compound with a suitable base such as sodium hydroxide preferably under an inert gas such as nitrogen at temperatures of about 0° to 50° C, preferably about 20°–25° C. A mercaptide of Formula (IIa) may also be prepared by similarly treating a compound of PA 790, filed even date herewith represented by the formula.

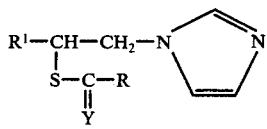

(VII)

wherein R, $R^1$ and Y have the same definition as in this application, but R in addition may be H or styryl. The compounds of Formula (VII) are particularly valuable when Y is O. As much of PA 790 as is pertinent is incorporated herein by reference. The thiocarbonyl chlorides useful in the process of this invention may be prepared by methods set forth in E. E. Reid, *Organic Chemistry of Bivalent Sulfur*, Vol. IV, Chemical Publishing Co., Inc., New York, New York (1962) while the carbonyl chlorides are prepared by following methods generally known in the art, e.g. M. Matzner et al., *Chemical Reviews*, 64, 645–687 (1964). As much of these references as is pertinent is incorporated herein by reference.

In the preparation of e.g., a mercaptide of Formula (IIa) wherein A is a suitable metal such as sodium, a compound of Formula (I) or an acid addition salt (e.g. oxalate of nitrate) wherein X is sulfur is reacted with a suitable metal hydroxide, e.g. an alkali metal hydroxide such as sodium hydroxide in a substantially inert solvent such as oxygenated hydrocarbon, for example, methanol, at temperatures of about 0° to 50° C. preferably about 20° to 25° to form e.g. the sodium thio salt. This salt may then be reacted with any suitable carbonyl chloride or thiocarbonyl chloride as discussed above to form the compounds of this invention represented by Formula (I) wherein X is S. The amount of alkali hydroxide needed for the reaction will depend in part on whether the compound represented by Formula (I) is a free base or the salt of a mono-basic acid (e.g. $HNO_3$) or a di-basic acid (e.g. oxalic acid). If the compound of Formula (I) is a free base at least 2 equivalents of the alkali hydroxide are required, while at least 3 equivalents, and preferably 3–4, are required if the compound (I) is the salt of a monobasic acid and at least 4, preferably 4–5, equivalents of the alkali hydroxide if the compound (I) is the salt of a di-basic acid.

Use of the Compounds of This Invention to Prepare Other Compounds

This process is based on the realization that certain compounds of the Formulae (II) or (IIa) may be reacted with an appropriate hydrocarbyl halide to give certain compounds disclosed in U.S. Ser. No. 593,620 filed July 7, 1975 and PA 791, filed even date herewith, that is certain novel 1-[β-($R^2$-thio)phenethyl]imidazoles represented by the formula

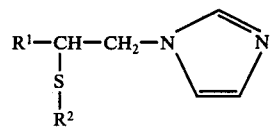

(VIII)

and the antimicrobial acid addition salts thereof, wherein $R^1$ is defined hereinbefore and $R^2$ is alkyl, alkenyl, aralkenyl, substituted aralkenyl, alkynyl, cycloalkyl, cycloalkyl alkyl, aralkyl, substituted aralkyl, or phenyl substituted with at least a nitro group at the 2- or 4-position, said substituted aralkenyl and substituted aralkyl containing at least one substituent on the aryl moiety selected from the group consisting of halo, lower alkyl, lower alkoxy, trifluoromethyl, nitro and cyano and said nitrophenyl optionally containing at least one other substituent selected from the group consisting of halo, lower alkyl, trifluoromethyl, nitro, and cyano.

This process is based on the reaction between the compounds of Formula (II) or a suitable acid (base) salt thereof and a suitable hydrocarbyl halide such as that set forth in the following reaction:

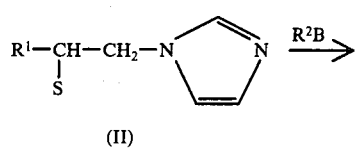

(II)

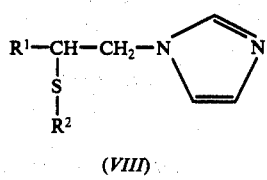

(VIII)

wherein R¹ and R² are as defined hereinbefore and B is a suitable leaving group such as mesylate, tosylate, or halo, e.g. bromo or preferably chloro.

Thus, one aspect of the process of this invention comprises preparing a compound of this invention represented by Formula (I) wherein X is S according to any of the processes set forth hereinbefore, converting this compound to a suitable compound represented by Formula (II), and reacting the latter compound with e.g. a suitable hydrocarbyl halide to form a compound of Formula (VIII). It is to be understood that the process may be carried out by (i) first forming a compound represented by Formula (II) or a suitable base salt thereof or (ii) by reacting a compound of Formula (I) (especially where X and Y are both S and Z is O) with a hydrocarbyl halide, (R²B), and a suitable base.

In the first case (i), a compound of this invention of Formula (I) or the acid addition salt, is reacted with a suitable base, e.g. an alkali metal hydroxide such as sodium hydroxide, potassium hydroxide or lithium hydroxide, and the like in a suitable solvent such as an oxygenated hydrocarbon e.g., methanol or ethanol, under an inert atmosphere for a time sufficient to convert the compound of this invention to the alkali metal base salt. Generally, this will take less than an hour at temperatures from 10° to about 50° C, preferably at about 15° to 25° C. Once the alkali metal base salt is obtained it is reacted with a suitable compound represented by (R²B) to give certain compounds of U.S. Ser. No. 593,620 or PA-791. The reaction between the R²B and the alkali metal base salt generally takes place in the presence of a suitable solvent at reaction temperatures of about 0° to 80° C, normally around 25°. Suitable solvents include methanol, ethanol, tetrahydrofuran, acetone and the like.

In the second case (ii) a compound of Formula (I) is reacted with a hydrocarbyl halide, particularly a chloride, and a suitable base such as an alkali metal hydroxide, e.g. sodium or potassium hydroxide, in an appropriate solvent such as methanol, ethanol, tetrahydrofuran, acetone or the like. It is believed that in this case the reaction proceeds through the intermediacy of a compound of Formulae (II) or (IIa) which is formed in situ. The temperature will generally be between about 0° and 80° C, preferably about 15°–25°, the reaction being completed in about 1 hour or less.

It has been further discovered that certain compounds of this invention of Formula (I) wherein X is S and Y and Z are O or S may be converted to the corresponding compound of Formula (VIII) having as the R² group a moiety the same as the R of Formula (I) by heating an appropriate compound of Formula (I), wherein X is S, as the free base either alone or in a suitable inert solvent such as polar organic solvents (e.g. acetonitrile, dimethylformamide, dimethylsulfoxide, ethanol, and the like) or non-polar organic solvents, e.g. toluene, at a temperature sufficient to form a compound of Formula (VIII). Generally this elevated temperature may range between about 50° and 200° C, but preferably will be about 50° to 100° C. Preferably Z is oxygen;

while Y may be oxygen or sulfur, it is preferably the latter. Generally, the reaction is completed in about 10 hours or less.

Preparation of Starting Materials

The following preparations are given to show one of skill in the art how to prepare the starting reactants for the process aspects of this invention.

Reaction Scheme A

In this reaction scheme the hydroxy compound of formula (III) is prepared by reduction of the corresponding ketone (IX) which in turn is prepared by reaction of an α-halo ketone with imidazole;

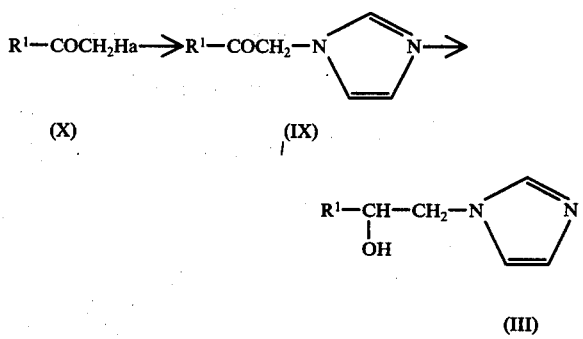

wherein Ha is chloro or bromo.

Certain α-halo ketones are available; others may be readily prepared by methods known in the art, for example, hy halogenation of the corresponding methyl ketone, from the Friedel-Crafts reaction or from acid halides, or enol ethers.

The α-halo ketone (X) is contacted with imidazole preferably in an inert organic solvent to afford the keto imidazole of Formula (IX). The reaction is carried out utilizing at least a molar amount and, preferably, an excess of imidazole relative to halo ketone. The reaction may be carried out in the absence of solvent or, preferably, in an inert organic solvent such as, for example, dimethylformamide, hexamethylphosphoramide, acetonitrile, and the like. The reaction is suitably carried out at a temperature initially between about −10° and 100° C, most preferably between about 0° and 25° C.

In the next step the keto imidazole of Formula (IX) is reduced to the hydroxy imidazole of Formula (III) utilizing a conventional metal hydride reducing agent such as, for example, sodium borohydride. The reaction is suitably carried out in an alcoholic solvent such as, for example, methanol or ethanol at a reduced temperature, for example, between about −10° and +25° C, most preferably about 0° C.

Other methods for preparing the 1-[β-hydroxyphenethyl] imidazole (III) may be apparent to those skilled in the art, such as methods described in Godefroi et al., *J. Med. Chem*, 12, 784–791 (1966), and U.S. Pat. No. 3,717,655 to Godefroi and Heeres.

Reaction Scheme B

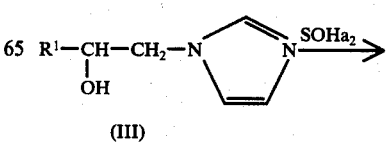

(III)

-continued

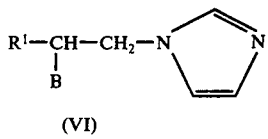

(VI)

In this reaction scheme the compound of Formula (III) is reacted with a thionyl halide of the formula SOHa$_2$ such as thionyl chloride or thionyl bromide to form a compound of Formula (VI), wherein B is halo. A suitable solvent such as chloroform or dichloromethane can be added to promote contact between the reactants at 0°-80° C, generally about 20° to reflux. The product can be isolated as the free base by evaporation of excess thionyl halide, addition of excess aqueous sodium or potassium carbonate, extraction with chloroform and removal of the solvent by vacuum distillation. Alternatively the product can be isolated as the corresponding hydrohalide salt by adding ethyl acetate or other inert liquid in which the salt is relatively insoluble q.s. precipitation.

EXAMPLES

The following specific examples are given to enable those skilled in the art to more clearly understand the practice of the present invention. These examples should not be considered as a limitation upon the scope of the invention but merely as being illustrative and representative thereof. In the examples that follow, experimental conditions such as reaction times, temperatures, etc. may be varied as is apparent to one of skill in the art. In enumerating compounds in the following examples, it is to be understood that the names represent the compound itself as well as the antimicrobial acid addition salts thereof, such as the nitrate or oxalate. Where appropriate for identification purposes, a representative salt is given with the corresponding melting point. In the case of an oxalate salt, there is one oxalate per imidazole, i.e., the salt is represented as

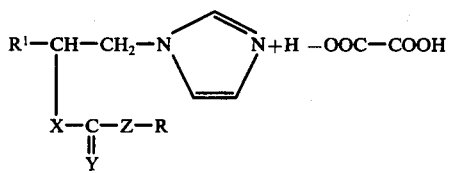

EXAMPLE 1

Preparation of 1-[β-(R-oxythiocarbonylthio)phenethyl]imidazoles

A. Preparation of 1-[2,4-dichloro-β-(ethoxythiocarbonyl)thio)phenethyl]imidazole Twenty grams of 1-(β, 2,4-trichlorophenethyl) imidazole hydrochloride was added to 300 milliliters (ml) of absolute ethanol and 25 grams of anhydrous potassium ethyl xanthate. The mixture was stirred at room temperature for about 3 days until the reaction was complete as indicated by thin layer chromatography. The solvent was removed, water added and the product extracted with ether. The extracts were washed with water, dried over magnesium sulfate and the ether evaporated. The resulting oil was purified by chromatography on silicia gel eluting with 15% acetone in dichloromethane. The resulting oil was then dissolved in ether and an ethereal solution of oxalic acid was added dropwise until precipitation was complete. Recrystallization of the precipitate from acetone provides the oxalate salt of 1-[2,4-dichloro-β-(ethoxythiocarbonylthio)phenethyl]imidazole as a white solid having a melting point of 122.5°-124° C. (foaming).

B. Preparation of other 1-[β-(R-oxythiocarbonylthio)phenethyl]imidazoles

Similarly by substituting other appropriate xanthates for potassium ethyl xanthate in part A of this example, the following imidazoles of this invention may be prepared, and, where indicated, may be characterized as the acid addition salts by treatment with the appropriate acid, e.g. nitric or oxalic:

1-[2,4-dichloro-β-(methoxythiocarbonylthio)phenethyl]imidazole;
1-[2,4-dichloro-β-(propoxythiocarbonylthio)phenethyl]imidazole;
1-[2,4-dichloro-β-(isopropoxythiocarbonylthio)-phenethyl]imidazole;
1-[2,4-dichloro-β-(n-butoxythiocarbonylthio)phenethyl]imidazole as nitrate salt, mp 120°-121.5° C (decomp.);
1-[2,4-dichloro-β-(isobutoxythiocarbonylthio)phenethyl]imidazole as nitrate salt, mp 148.5°-150° C (decomp.);
1-[2,4-dichloro-β-(n-pentyloxythiocarbonylthio)-phenethyl]imidazole; as nitrate salt, mp 118.5°-119.5° C (decomp.) (foaming);
1-[2,4-dichloro-β-(isopentyloxythiocarbonylthio)-phenethyl]imidazole;
1-[2,4-dichloro-β-(n-hexyloxythiocarbonylthio)-phenethyl]imidazole;
1-[2,4-dichloro-β-(n-heptyloxythiocarbonylthio)-phenethyl]imidazole;
1-[2,4-dichloro-β-(n-octyloxythiocarbonylthio)-phenethyl]imidazole as nitrate salt, mp 107°-113° C (decomp.-foaming);
1-[2,4-dichloro-β-(t-butoxythiocarbonylthio)phenethyl]imidazole;
1-[2,4-dichloro-β-(benzyloxythiocarbonylthio)phenethyl]imidazole as oxalate salt, mp 107°-110° C (decomp);
1[2,4-dichloro-β-(p-fluorobenzyloxythiocarbonylthio)phenethyl]imidazole;
1-[2,4-dichloro-β-(p-chlorobenzyloxythiocarbonylthio)phenethyl]imidazole;
1-[2,4-dichloro-β-(p-bromobenzyloxythiocarbonylthio)phenethyl]imidazole;
1-[2,4-dichloro-β-(p-methylbenzyloxythiocarbonylthio)phenethyl]imidazole;
1-[2,4-dichloro-β-(3-phenyl-2-propenyloxythiocarbonylthio)-phenethyl]imidazole;
1-[2,4-dichloro-β-(3-p-chlorophenyl-2-propenyloxythiocarbonyl-thio)phenethyl]imidazole;
1-[2,4-dichloro-β-(o-chlorobenzyloxythiocarbonylthio)phenethyl]imidazole;
1-[2,4-dichloro-β-(m-chlorobenzyloxythiocarbonylthio)phenethyl]imidazole;
1-[2,4-dichloro-β-(2,4-dichlorobenzyloxythiocarbonylthio)-phenethyl]imidazole;
1-[2,4-dichloro-β-(3,4-dichlorobenzyloxythiocarbonylthio)phenethyl]imidazole;
1-[2,4-dichloro-β-(cyclohexyloxythiocarbonylthio)-phenethyl]imidazole as a nitrate salt, mp 139.5°-140.5° C (decomp-foaming);

1-[2,4-dichloro-β-(cyclohexylmethoxythiocarbonyl-
thio)phenethyl]imidazole;
and the like.

C. Preparation of other imidazoles having different $R^1$ substituents

Similarly by substituting other 1-[β-halophenethyl-
]imidazoles for 1[β,2,4-trichlorophenethyl]imidazole
hydrochloride and other appropriate xanthates for ethyl
xanthate in Part A of this example other compounds of
this invention may be prepared such as the following:

1[4-chloro-β-(methoxythiocarbonylthio)phenethyl-
]imidazole;
1-[2,4-difluoro-β-(n-butoxythiocarbonylthio)phene-
thyl]imidazole;
1-[4-fluoro-β-(n-hexyloxythiocarbonylthio)phene-
thyl]imidazole;
1-[2,4,6-trichloro-β-(benzyloxythiocarbonylthio)-
phenethyl]imidazole;
1[-4-methyl-β-(isopropoxythiocarbonylthio)phene-
thyl]imidazole;
1-[4-trifluoromethyl-β-(p-butoxythiocarbonylthio)-
phenethyl]imidazole;
1-]2,4-dimethyl-β-(ethoxythiocarbonylthio)phene-
thyl]imidazole;
1-[4-chloro-β-(p-chlorobenzyloxythiocarbonylthio)-
phenethyl]imidazole;
1-[4-chloro-β-(p-bromobenzyloxythiocarbonylthio)-
phenethyl]imidazole;
1-[4-chloro-β-(ethoxythiocarbonylthio)phenethyl-
]imidazole;
1-[4-chloro-β-(n-propoxythiocarbonylthio)phene-
thyl]imidazole;
1-[4-chloro-β-(t-butoxythiocarbonylthio)phenethyl-
]imidazole;
1-[4-chloro-β-(n-pentyloxythiocarbonylthio)phene-
thyl]imidazole;
1-[4-bromo-β-(p-chlorobenzyloxythiocarbonylthio)-
phenethyl]imidazole;
1-[β-(cyclohexyloxythiocarbonylthio)phenethyl-
]imidazole;
1-[2,4,6-trichloro-β-(methoxythiocarbonylthiol-
phenethyl]
1[2,4,6-trichloro-β-(n-propoxythiocarbonylthio)-
phenethyl]imidazole;
1-[2,4,6-trichloro-β-(isopropoxythiocarbonylthio)-
phenethyl]imidazole;
1-[2,4,6-trichloro-β-(ethoxythiocarbonylthio)phene-
thyl]imidazole;
1-[β-(n-hexyloxythiocarbonylthio)phenethyl-
]imidazole;
1-[2,4,6-trichloro-β-(p-fluorobenzyloxythiocarbonyl-
thio)phenethyl]imidazole;
1-[2,4,6-trichloro-β-(p-chlorobenzyloxythiocarbonyl-
thio)phenethyl]imidazole;
1-[2,4-dibromo-β-(n-propoxythiocarbonylthio)phene-
thyl]imidazole;
1-[2,4-dibromo-β-(p-methylbenzyloxythiocarbonyl-
thio)phenethyl]imidazole;
1-[2,4-dibromo-β-(p-chlorobenzyloxythiocarbonyl-
thio)phenethyl]imidazole;
1-[2,4-difluoro-β-(n-pentyloxythiocarbonylthio)-
phenethyl]imidazole;
1-[2,4-difluoro-β-(n-hexyloxythiocarbonylthio)-
phenethyl]imidazole;
1-[2,4-difluoro-β-(p-chlorobenzyloxythiocarbonylthi-
o)phenethyl]imidazole;
1-[2,4-dimethyl-β-(n-pentyloxythiocarbonylthio)-
phenethyl]imidazole;
1-[3,4-dichloro-β-(n-propoxythiocarbonylthio)phene-
thyl]imidazole;
1-[2,4,6-trimethyl-β-(t-butoxythiocarbonylthio)-
phenethyl]imidazole;
1-[4-t-butyl-β-(ethoxythiocarbonylthio)phenethyl-
]imidazole;
1-[4-trifluoromethyl-β-methoxythiocarbonylthio)-
phenethyl]imidazole;
1-[2,4,6-trimethyl-β-(ethoxythiocarbonylthio)phene-
thyl]imidazole as nitrate salt, mp 134°–136° C (de-
comp-foaming);
1-[4-t-butyl-2,6-dimethyl-β-(methoxythiocarbonylthi-
o)phenethyl]imidazole,
and the like.

EXAMPLE 2

Preparation of
1-[β-(R-oxycarbonylthio)phenethyl]imidazoles

A. Preparation of 1-[2,4-dichloro-β-(n-octyloxycar-
bonylthio)phenethyl]imidazole By following the procedure set forth in Example 1,
part A, but substituting S-potassium O-octyl thiocar-
bonate for potassium ethyl xanthate, 1-[2,4-dichloro-β-
(n-octyloxycarbonylthio)phenethyl]imidazole may be
prepared. The nitrate salt of the resulting oil is formed
by dropwise addition of nitric acid ($d = 1.42$) to an
ethereal solution of the imidazole until precipitation is
complete. Filtration and recrystallization from ethyl
acetate gives the nitrate salt having a melting point of
99°–101° C.

B. By following the procedure set forth in part A of this
example, but substituting other appropriate S-potassium
O-hydrocarbyl thiocarbonates, other 1-[2,4-dichloro-β-
(R-oxycarbonylthio)phenethyl]imidazoles are prepared
such as 1-[2,4-dichloro-β-(isopropoxycarbonylthio)-
phenethyl]imidazole; 1-[2,4-dichloro-β-(n-propoxycar-
bonylthio)phenethyl]imidazole; and the like.

C. Other imidazoles of Formula (I) having different $R^1$
substituents may be similarly prepared by substituting
other 1-[β-halo phenethyl]imidazoles for 1-[β,2,4-tri-
chlorophenethyl]imidazole hydrochloride and other
S-potassium O-hydrocarbyl thiocarbonates for S-potas-
sium O-octyl thiocarbonate in part A of this example.
Other imidazoles of this invention include compounds
such as: 1-[4-chloro-β-(isobutoxycarbonylthio)phene-
thyl]imidazole; 1-[4-chloro-β-(n-butoxycarbonylthio)-
phenethyl]imidazole; and the like.

EXAMPLE 3

Preparation of
1-[β-(R-oxycarbonylthio)phenethyl]imidazoles

A. Preparation of 1-[2,4-dichloro-β-(n-butoxycarbonyl-
thio)phenethyl]imidazole

As an alternative to the process of Example 2, the
following procedure, which is analagous to Example 5,
may be used:

To a solution of 0.16 g ($4.0 \times 10^{-3}$ mole) of sodium
hydroxide in 40 ml of anhydrous methanol under nitro-
gen was added 0.42 g ($1.0 \times 10^{-3}$ mole) of 1-[2,4-
dichloro-β-(ethoxythiocarbonylthio)phenethyl-
]imidazole nitrate. After stirring for 45 minutes at room
temperature, 1.0 g anhydrous potassium carbonate
($K_2CO_3$) and 1 ml of n-butyl chloroformate were added
and the mixture was stirred for 4 additional hours at
room temperature under nitrogen. After removing the solvent in vacuo, water was added and the residue extracted with ether. The extracts were washed with water, dried (MgSO₄) and the nitrate salt of 1-[2,4-dichloro-β-(n-butoxycarbonylthio)phenethyl]imidazole precipitated and recrystallized from ethyl acetate, mp 112.5°–114.5° C (decomp).

B. By following a procedure similar to part A of this example, but substituting other R chloroformates for n-butyl chloroformate and using appropriate conditions, other 1-[2,4-dichloro-β-(R-oxycarbonylthio)-phenethyl]imidazoles may be prepared, such as 1-[2,4-dichloro-β-(ethoxycarbonylthio)phenethyl]imidazole;

1-[2,4-dichloro-β-(n-pentyloxycarbonylthio)phenethyl]imidazole;
1-[2,4-dichloro-β-(n-hexyloxycarbonylthio)phenethyl]imidazole;
1-[2,4-dichloro-β-(n-heptyloxycarbonylthio)phenethyl]imidazole;
1-[2,4-dichloro-β-(2,4-dichlorophenoxycarbonylthio)phenethyl]imidazole;
1-[2,4-dichloro-β-(3,4-dichlorophenoxycarbonylthio)phenethyl]imidazole;
1-[2,4-dichloro-β-(p-chlorophenoxycarbonylthio)-phenethyl]imidazole;
1-[2,4-dichloro-β-(p-chlorobenzyloxycarbonylthio)-phenethyl]imidazole;
1-[2,4-dichloro-β-(2,4-dichlorobenzyloxycarbonylthio)phenethyl]imidazole;
1-[2,4-dichloro-β-(3,4-dichlorobenzyloxycarbonylthio)phenethyl]imidazole;
1-[2,4-dichloro-β-(p-methylbenzyloxycarbonylthio)-phenethyl]imidazole;
1-[2,4-dichloro-β-(3-phenyl-2-propenyloxycarbonylthio)phenethyl]imidazole;
and the like.

C. Other imidazoles of Formula (I) having different R¹ substituents may be similarly prepared by substituting other 1-[β-(R-oxythiocarbonylthio)phenethyl]imidazoles for 1-[2,4-dichloro-β-(ethoxythiocarbonylthio)phenethyl]imidazole and other appropriate R-chloroformate for n-butyl chloroformate in part A of this example. These include 1-[4-chloro-β-(n-pentyloxycarbonylthio)phenethylimidazole;
1-[4-chloro-β-(n-hexyloxycarbonylthio)phenethylimidazole;
1-[4-chloro-β-(n-heptyloxycarbonylthio)phenethylimidazole;
1-[4-chloro-β-(n-octyloxycarbonylthio)phenethylimidazole;
1-[4-chloro-β-(3,4-dichlorophenoxycarbonylthio)-phenethyl]imidazole;
1-[4-chloro-β-(2,4-dichlorophenoxycarbonylthio)-phenethyl]-
1-[4-chloro-β-(p-methylphenylpropoxycarbonylthio)phenethyl]imidazole;
1-[4-chloro-β-(3,4-dichlorobenzyloxycarbonylthio)-phenethyl]imidazole;
1-[4-chloro-β-(2,4-dichlorobenzyloxycarbonylthio)-phenethyl]imidazole;
1-[4-chloro-β-(o-n-propylphenoxycarbonylthio)-phenethyl]imidazole;
1-[4-bromo-β-(p-ethylbenzyloxycarbonylthio)phenethyl]imidazole;
1-[β-(n-decyloxycarbonylthio)phenethyl]imidazole;
1-[2,4-dimethyl-β-(3,4,5-trichlorophenoxycarbonylthio)phenethyl]imidazole;
1-[4-t-butyl-β-(3,4-methylbromophenoxycarbonylthio)phenethyl]imidazole,
and the like.

EXAMPLE 4

Preparation of 1-[β-(phenoxythiocarbonylthio)phenethyl]imidazoles

A. Preparation of 1-[2,4-dichloro-β-p-chlorophenoxythiocarbonylthio)phenethyl]imidazole By following the procedure set forth in Example 3 but using O-p-chlorophenyl chlorothioformate in place of n-butyl chloroformate, and employing the appropriate reaction conditions, the nitrate salt of 1-[2,4-dichloro-β-(p-chlorophenoxythiocarbonylthio)phenethyl]imidazole is prepared.

B. By substituting other appropriate O-phenyl chlorothioformates for p-chlorophenyl chlorothioformate in part A of this example and adjusting the reaction conditions as needed, other 1-[2,4-dichloro-β-(phenoxythiocarbonylthio)phenethyl]imidazoles may be prepared such as 1-[2,4-dichloro-β-(phenoxythiocarbonylthio)phenethyl]imidazole;
1-[2,4-dichloro-β-(p-fluorophenoxythiocarbonylthio)phenethyl]-imidazole;
1-[2,4-dichloro-β-(p-bromophenoxythiocarbonylthio)phenethyl]imidazole;
1-[2,4-dichloro-β-(3,4-dichlorophenoxythiocarbonylthio)phenethyl]imidazole;
1-[2,4-dichloro-β-(2,4-dichlorophenoxythiocarbonylthio)phenethyl]imidazole;
1-[2,4-dichloro-β-(m-chlorophenoxythiocarbonylthio)phenethyl]imidazole;
1-[2,4-dichloro-β-(o-chlorophenoxythiocarbonylthio)phenethyl]imidazole;
1-[2,4-β-(p-methylphenoxythiocarbonylthio)phenethyl]imidazole;
1-[2,4-dichloro-β-(o-methylphenoxythiocarbonylthio)phenethyl]imidazole;
1-[2,4-dichloro-β-(p-ethylphenoxythiocarbonylthio)-phenethyl]imidazole;

C. Similarly, by following the procedure of parts A and B of this example but utilizing an appropriate substituted O-phenyl chlorothioformate and substituting another 1-[β-(R-oxythiocarbonylthio)phenethyl]imidazole of Formula (I) having a different R¹ substituent for 1-[2,4-dichloro-β-(ethoxythiocarbonylthio)-phenethyl]imidazole, other compounds of this invention are prepared such as 1-(2,4-β-(phenoxythiocarbonylthio)phenethyl]imidazole;
1-[4-bromo-β-(2,4-dichlorophenoxythiocarbonylthio)phenethyl]imidazole;
1-[4-chloro-β-(3,4-dichlorophenoxythiocarbonylthio)phenethyl]imidazole;
1-[4-chloro-β-(2,4-dichlorophenoxythiocarbonylthio)phenethyl]imidazole;
1-[4-chloro-β-(p-chlorophenoxythiocarbonylthio)-phenethyl]imidazole;
1-[2,4,6-trichloro-β-(p-fluorophenoxythiocarbonylthio)phenethyl]imidazole;
1-[2,4,6-trichloro-β-(phenoxythiocarbonylthio)-phenethyl]imidazole;
1-[2,4,6-trichloro-β-(p-chlorophenoxythiocarbonylthio)phenethyl]imidazole;
1-[2,4-dibromo-β-(p-chlorophenoxythiocarbonylthio)phenethyl]imidazole;

1-[2,4,6-trimethyl-β-(p-chlorophenoxythiocarbonyl-thio)phenethyl]imidazole,
and the like.

EXAMPLE 5

Preparation of
1-[β-(R-thiocarbonylthio)phenethyl]imidazoles

A. 1-[2,4-dichloro-β-(ethoxythiocarbonylthio)phenethyl]imidazole oxalate (450 mg) prepared as described in Example 1, part A, was added under nitrogen to a stirred solution of 200 mg sodium hydroxide in 30 ml methanol at room temperature. Stirring was continued until the reaction was complete as indicated by thin layer chromatography (approximately 20 minutes) and the resulting 1-[2,4-dichloro-β-(sodium thio)-phenethyl]imidazole was reacted with a slight excess of t-butylthiolchloroformate by adding the chloroformate directly to the sodium salt solution. The mixture was stirred for 30 minutes, and the solvent removed by evaporation. Ether (150 ml) was added to the residue and the mixture was washed with three 30 ml portions of water, then dried over magnesium sulfate. The solution was then concentrated and treated with nitric acid ($d$ = 1.42) until precipitation of the nitrate salt was complete. Recrystallization from ethyl acetate/acetone gave snow-white microcrystals of the nitrate salt of 1-[2,4-dichloro-β-(t-butylthiolcarbonylthio)phenethyl]imidazole, mp 163°–166.5° (decomp.-foaming).

B. By following the procedure set forth in part A of this example but employing the appropriately substituted R-thiol chloroformate in place of the t-butylthiolchloroformate other R-thiolcarbonylthio substituted compounds may be prepared. These compounds include the following:

1-[2,4-dichloro-β-(ethylthiolcarbonylthio)phenethyl]imidazole;
1-[2,4-dichloro-β-(n-propylthiolcarbonylthio)phenethyl]imidazole;
1-[2,4-dichloro-β-(isopropylthiolcarbonylthio)phenethyl]imidazole;
1-[2,4-dichloro-β-(n-butylthiolcarbonylthio)phenethyl]imidazole;
1-[2,4-dichloro-β-(isobutylthiolcarbonylthio)phenethyl]imidazole;
1-[2,4-dichloro-β-(n-pentylthiolcarbonylthio)phenethyl]imidazole;
1-[2,4-dichloro-β-(n-hexylthiolcarbonylthio)phenethyl]imidazole;
1-[2,4-dichloro-β-(n-heptylthiolcarbonylthio)phenethyl]imidazole;
1-[2,4-dichloro-β-(p-chlorophenylthiolcarbonylthio)phenethyl]imidazole;
1-[2,4-dichloro-β-(p-fluorophenylthiolcarbonylthio)phenethyl]imidazole;
1-[2,4-dichloro-β-(phenylthiolcarbonylthio)phenethyl]imidazole as nitrate salt, mp 157.5°–160.5° C (decomp.-foaming);
1-[2,4-dichloro-β-(2,4-dichlorophenylthiolocarbonylthio)phenethyl]imidazole;
1-[2,4-dichloro-β-(3,4-dichlorophenylthiolcarbonylthio)phenethyl]imidazole;
1-[2,4-dichloro-β-(benzylthiolcarbonylthio)phenethyl]imidazole;
1-[2,4-dichloro-β-(p-fluorobenzylthiolcarbonylthio)phenethyl]imidazole;
1-[2,4-dichloro-β-(p-chlorobenzylthiolcarbonylthio)phenethyl]imidazole; and
1-[2,4-dichloro-β-(3-phenyl-2-propenylthiolcarbonylthio)phenethyl]imidazole.

C. Similarly, by utilizing compounds related to or the same as those set forth in Example 1, parts B and C, the corresponding sodium salts can be obtained and reacted with the appropriately substituted R-thiol chloroformate to yield other compounds of this invention such as:

1-[4-chloro-β-(n-butylthiolcarbonylthio)phenethyl]imidazole;
1-[4-bromo-β-(isopropylthiolcarbonylthio)phenethyl]imidazole;
1-[4-fluoro-β-(n-hexylthiolcarbonylthio)phenethyl]imidazole;
1-[2,4,6-trichloro-β-(phenylthiolcarbonylthio)phenethyl]imidazole;
1-[2,4-dimethyl-β-(p-chlorophenylthiolcarbonylthio)phenethyl]imidazole; and
1-[4-t-butyl-β-(ethylthiolcarbonylthio)phenethyl]imidazole.

EXAMPLE 6

Preparation of
1-[β-(R-thiolthiocarbonylthio)phenethyl]imidazoles

A. By following the procedure set forth in Example 1, part A, 1-[2,4-dichloro-β-(ethylthiolthiocarbonylthio)-phenethyl]imidazole may be prepared by utilizing potassium ethyl trithiocarbonate in place of potassium ethyl xanthate and employing appropriate experimental conditions.

B. Compounds similar to those set forth in part A of this example may be prepared by this method as well by substituting the appropriate metal hydrocarbyl trithiocarbonate for the potassium ethyl xanthate of part A of Example 1. Compounds made by this method include the following:

1-[2,4-dichloro-β-(n-propylthiolthiocarbonylthio)-phenethyl]imidazole;
1-[2,4-dichloro-β-(n-butylthiolthiocarbonylthio)-phenethyl]imidazole;
1-[2,4-dichloro-β-(t-butylthiolthiocarbonylthio)-phenethyl]imidazole;
1-[2,4-dichloro-β-(n-pentylthiolthiocarbonylthio)-phenethyl]imidazole;
1-[2,4-dichloro-β-(isopropylthiolthiocarbonylthio)-phenethyl]imidazole;
1-[2,4-dichloro-β-(benzylthiolthiocarbonylthio)-phenethyl]imidazole;
1-[2,4-dichloro-β-(p-fluorobenzylthiolthiocarbonylthio)phenethyl]imidazole; and
1-[2,4-dichloro-β-(p-chlorobenzylthiolthiocarbonylthio)phenethyl]imidazole.

C. Similarly, by following the procedure set forth in Example 1, parts A and C, but employing 1-[β-halophenethyl]imidazoles having different R¹ substituents in place of the 1-[β,2,4-trichlorophenethyl]imidazole hydrochloride of part A of Example 1 and utilizing the appropriate metal hydrocarbyl trithiocarbonate similar to those of Example 6, part B, in place of potassium ethyl xanthate of Example 1, part A, the following compounds are prepared:

1-[β-(t-butylthiolthiocarbonylthio)phenethyl]imidazole;
1-[4-chloro-β-(p-fluorobenzylthiolthiocarbonylthio)-phenethyl]imidazole;
1-[4-chloro-β-(p-chlorobenzylthiolthiocarbonylthio)-phenethyl]imidazole;

1-[4-chloro-β-(ethylthiolthiocarbonylthio)phenethyl]imidazole;
1-[4-chloro-β-(n-propylthiolthiocarbonylthio)phenethyl]imidazole;
1-[4-chloro-β-(ethylthiolthiocarbonylthio)phenethyl]imidazole;
1-[4-chloro-β-(n-propylthiolthiocarbonylthio)phenethyl]imidazole;

Alternative route to
1-[β-(R-thiolthiocarbonylthio)phenethyl]imidazoles

A. Preparation of 1-[2,4-dichloro-β-(methylthiolthiocarbonylthio)phenethyl]imidazole By following the procedure set forth in Example 3 but using methyl chlorodithioformate in place of n-butyl chloroformate, and employing the appropriate reaction conditions, the nitrate salt of 1-[2,4-dichloro-β-(methylthiolthiocarbonylthio)phenethyl]imidazole is prepared.

B. By substituting other appropriate R chlorodithioformates for methyl chlorodithioformate in part A of this example and adjusting the reaction conditions as needed, other 1-[2,4-dichloro-β-(R-thiolthiocarbonylthio)phenethyl]imidazoles may be prepared such as 1-[2,4-dichloro-β-(ethylthiolthiocarbonylthio)imidazole;
1-[2,4-dichloro-β-(phenylthiolthiocarbonylthio)phenethyl]imidazole;
1-[2,4-dichloro-β-(p-fluorophenylthiolthiocarbonylthio)phenethyl]imidazole;
1-[2,4-dichloro-β-(p-chlorophenylthiolthiocarbonylthio)phenethyl]imidazole;

and the like.

C. Similarly, by following the procedure of parts A and B of this example but utilizing an appropriate R chlorodithioformate and substituting another 1-[β-(R-oxythiocarbonylthio)phenethyl]imidazole of formula (I) having a different R¹ substituent for 1-[2,4-dichloro-β-(ethoxythiocarbonylthio)phenethyl]imidazole, other compounds of this invention may be prepared such as 1-[4-chloro-β-(methylthiolthiocarbonylthio)phenethyl]imidazole;
1-[4-chloro-β-(ethylthiolthiocarbonylthio)phenethyl]imidazole;
1-[4-chloro-β-(phenylthiolthiocarbonylthio)phenethyl]imidazole;
1-[4-bromo-β-(ethylthiolthiocarbonylthio)phenethyl]imidazole;
1-[4-chloro-β-(p-chlorophenylthiolthiocarbonylthio)phenethyl]imidazole;
1-[2,4-dimethyl-β-(p-bromophenylthiolthiocarbonylthio)phenethyl]imidazole;
1-[4-chloro-β-(p-fluorophenylthiolthiocarbonylthio)phenethyl]imidazole and the like.

EXAMPLE 8

Preparation of
1-[β-(R-oxycarbonyloxy)phenethyl]imidazoles

A. A solution of 0.8g (4.86 × 10⁻³ moles) of n-hexylchloroformate in 10 ml of dry tetrahydrofuran was added dropwise to a 0° C solution of 1.0 g (3.98 × 10⁻³ moles) of 1-[β-hydroxy-2,4-dichlorophenethyl]imidazole, 2 ml of triethylamine, and 30 ml of dry tetrahydrofuran over a period of 10 minutes. After stirring the resulting white suspension for 2 hours at room temperature, the solvent was removed, water added and the solution extracted with ether. The extracts were washed with water, dried (MgSO₄) and the nitrate salt precipitated by dropwise addition of concentrated nitric acid (d = 1.42) until precipitation was complete. After filtering, 0.62g of the nitrate salt of 1-[2,4-dichloro-β-(n-hexyloxycarbonyloxy)phenethyl]imidazole, was recrystallized from ethyl acetate/ethanol, mp 108°–112° C (decomp).

B. By following the procedure set forth in part A of this example but employing a different hydrocarbyl chloroformate, other compounds of this invention may be prepared, such as:

1-[2,4-dichloro-β-(n-butoxycarbonyloxy)phenethyl]imidazole;
1-[2,4-dichloro-β-(n-pentyloxycarbonyloxy)phenethyl]imidazole;
1-[2,4-dichloro-β-(n-heptyloxycarbonyloxy)phenethyl]imidazole;
1-[2,4-dichloro-β-(n-octyloxycarbonyloxy)phenethyl]imidazole as nitrate salt, mp 92.5°–95.5° C (decomp).
1-[2,4-dichloro-β-(n-nonyloxycarbonyloxy)phenethyl]imidazole;
1-[2,4-dichloro-β-(3-p-chlorophenylpropoxycarbonyloxy)phenethyl]imidazole;
1-[2,4-dichloro-β-(2,4-dichlorophenoxycarbonyloxy)phenethyl]imidazole;
1-[2,4-dichloro-β-(p-chlorophenoxycarbonyloxy)phenethyl]imidazole;
1-[2,4-dichloro-β-(p-chlorooxycarbonyloxy)phenethyl]imidazole;
1-[2,4-dichloro-β-(3,4-dichlorobenzyloxycarbonyloxy)phenethyl]imidazole; and
1-[2,4-dichloro-β-(2,4-dichlorobenzyloxycarbonyloxy)phenethyl]imidazole.

C. By following the procedure of part A of this example but employing a different hydrocarbyl chloroformate as well as a different 1-(β-hydroxyphenethyl)imidazole, other compounds of this invention may be prepared, such as:

1-[4-chloro-β-(n-heptyloxycarbonyloxy)phenethyl]imidazole;
1-[4-chloro-β-(cyclopentylmethoxycarbonyloxy)phenethyl]imidazole;
1-[4-bromo-β-(cyclooctylethoxycarbonyloxy)phenethyl]imidazole;
1-[4-chloro-β-(p-chlorophenoxycarbonyloxy)phenethyl]imidazole as oxalate salt, mp 152°–152.5° C (decomp.-foaming);
1-[β-(3-p-tert-butylphenylpropoxycarbonyloxy)phenethyl]imidazole;
1-[4-trifluoromethyl-β-(2,4-dichlorophenoxycarbonyloxy)phenethyl]imidazole;
1-[4-t-butyl-β-(p-chlorophenoxycarbonyloxy)phenethyl]imidazole;
1-[2,4-dimethyl-β-(2,4,6-trichlorophenoxycarbonyloxy)phenethyl]imidazole;
1-[β-(n-dodecyloxycarbonyloxy)phenethyl]imidazole;
1-[4-chloro-β-(p-tert-butylphenoxycarbonyloxy)phenethyl]imidazole;
1-[4-fluoro-β-(p-tert-butylbenzyloxycarbonyloxy)phenethyl]imidazole;

and the like.

EXAMPLE 9

Preparation of
1-[β-(R-oxythiocarbonyloxy)phenethyl]imidazoles

A. Two hundred forty mg of a dispersion of 56% w sodium hydride in mineral oil is added to 1.30g of 1-[2,4-dichloro-β-hydroxyphenethyl]imidazole in 10 ml. hexamethylphosphoramide under nitrogen and the mixture stirred at 10°-25° C for 1 hour and at 50° C for a further 1 hour. The resulting solution is then cooled to ca. 5° C. and treated dropwise with 685mg. of O-ethyl chlorothioformate and the mixture stirred 1 hour at room temperature and at 40° for 1-2 hours. The mixture is poured into water, extracted with ether and the extracts washed with water, dried over magnesium sulfate and evaporated. The product is purified by chromatography on silica gel eluting with 10-15% acetone in dichloromethane.

The oxalate salt is precipitated by addition of ethereal oxalic acid to the product in ether until precipitation is complete. Recrystallization from ethyl acetate/acetone gives crystals of 1-[2,4-dichloro-β-(ethoxythiocarbonyloxy)phenethyl]imidazole oxalate.

B. By following the procedure of part A of this example but employing other appropriate O-hydrocarbyl chlorothioformates, the following products may be prepared:
 1-[2,4-dichloro-β-(n-propoxythiocarbonyloxy)phenethyl]imidazole;
 1-[2,4-dichloro-β-(n-butoxythiocarbonyloxy)phenethyl]imidazole;
 1-[2,4-dichloro-β-(n-pentyloxythiocarbonyloxy)phenethyl]imidazole;
 1-[2,4-dichloro-β-(n-hexyloxythiocarbonyloxy)phenethyl]imidazole;
 1-[2,4-dichloro-β-(n-heptyloxythiocarbonyloxy)phenethyl]imidazole;
 1-[2,4-dichloro-β-(p-chlorophenoxythiocarbonyloxy)phenethyl]imidazole;
 1-[2,4-dichloro-β-(2,4-dichlorophenoxythiocarbonyloxy)phenethyl]imidazole;
 1-[2,4-dichloro-β-(3,4-dichlorophenoxythiocarbonyloxy)phenethyl]imidazole;
 1-[2,4-dichloro-β-(p-chlorobenzyloxythiocarbonyloxy)phenethyl]imidazole;
 1-[2,4-dichloro-β-(2,4-dichlorobenzyloxythiocarbonyloxy)phenethyl]imidazole; and
 1-[2,4-dichloro-β-(3,4-dichlorobenzyloxythiocarbonyloxy)phenethyl]imidazole.

C. Similarly, by following the procedure of part A of this example but employing 1-[β-hydroxyphenethyl]imidazoles of Formula (III) having different R¹ substituents and also employing different O-hydrocarbyl chlorothioformates, the following compounds are prepared:
 1-[4-t-butyl-β-(p-chlorobenzyloxythiocarbonyloxy)phenethyl]imidazole;
 1-[β-(2,3,4,5,6-pentachlorophenoxythiocarbonyloxy)phenethyl]imidazole;
 1-[4-chloro-β-(2,4-dichlorophenoxythiocarbonyloxy)phenethyl]imidazole;
 1-[2,4-dibromo-β-(ethoxythiocarbonyloxy)phenethyl]imidazole;
and the like.

EXAMPLE 10

Preparation of
1-[β-(R-thiolthiocarbonyloxy)phenethyl]imidazoles

A. By a similar procedure to that described in Example 9, part A, the sodium salt of 1-[2,4-dichloro-β-hydroxyphenethyl]imidazole is prepared which is then reacted with methyl chlorodithioformate to form 1-[2,4-dichloro-β-(methylthiolthiocarbonyloxy)phenethyl]imidazole.

B. By substituting other appropriate hydrocarbyl chlorodithioformates for methyl chlorodithioformate in part A of this example, the following compounds may be prepared:
 1-[2,4-dichloro-β-(ethylthiolthiocarbonyloxy)phenethyl]imidazole;
 1-[2,4-dichloro-β-(n-propylthiolthiocarbonyloxy)phenethyl]imidazole;
 1-[2,4-dichloro-β-(n-butylthiolthiocarbonyloxy)phenethyl]imidazole;
 1-[2,4-dichloro-β-(n-pentylthiolthiocarbonyloxy)phenethyl]imidazole;
 1-[2,4-dichloro-β-(n-hexylthiolthiocarbonyloxy)phenethyl]imidazole;
 1-[2,4-dichloro-β-(n-heptylthiolthiocarbonyloxy)phenethyl]imidazole;
 1-[2,4-dichloro-β-(p-chlorophenylthiolthiocarbonyloxy)phenethyl]imidazole;
 1-[2,4-dichloro-β-(p-fluorophenylthiolthiocarbonyloxy)phenethyl]imidazole; and
 1-[2,4-dichloro-β-(p-chlorobenzylthiolthiocarbonyloxy)phenethyl]imidazole.

C. Similarly, by following the procedure of part A of this example but employing a 1-[β-hydroxyphenethyl]imidazole of Formula (III) having different R¹ substituents and also employing different hydrocarbyl chlorodithioformates, the following compounds are prepared:
 1-[4-t-butyl-β-(p-chlorobenzylthiolthiocarbonyloxy)phenethyl]imidazole;
 1-[β-(2,3,4,5,6-pentachlorophenylthiolthiocarbonyloxy)phenethyl]imidazole;
 1-[4-chloro-β-(2,4-dichlorophenylthiolthiocarbonyloxy)phenethyl]imidazole;
 1-[2,4-dibromo-β-(ethylthiolthiocarbonyloxy)phenethyl]imidazole;
and the like.

EXAMPLE 11

Preparation of 1-[β-(R-thiolcarbonyloxy)phenethyl imidazoles

A. By following the procedure of Example 9, part A, the sodium salt of 1-[2,4-dichloro-β-hydroxyphenethyl]imidazole is prepared which is then reacted with S-ethyl chlorothioformate to form 1-[2,4-(ethylthiolcarbonyloxy)phenethyl]imidazole.

B. By substituting other appropriate S-hydrocarbyl chlorothioformates for S-ethyl chlorothioformate in part A of this example, the following compounds may be prepared:
 1-[2,4-dichloro-β-(n-propylthiolcarbonyloxy)phenethyl]imidazole;
 1-[2,4-dichloro-β-(n-butylthiolcarbonyloxy)phenethyl]imidazole;
 1-[2,4-dichloro-β-(n-pentylthiolcarbonyloxy)phenethyl]imidazole;
 1-[2,4-dichloro-β-(n-hexylthiolcarbonyloxy)phenethyl]imidazole;

1-[2,4-dichloro-β-(n-heptylthiolcarbonyloxy)phenethyl]imidazole;

1-[2,4-dichloro-β-(p-chlorophenylthiolcarbonyloxy)phenethyl imidazole;

1-[2,4-dichloro-β-(2,4-dichlorophenylthiolcarbonyloxy)phenethyl]imidazole;

1-[2,4-dichloro-β-(3,4-dichlorophenylthiolcarbonyloxy)phenethyl]imidazole;

1-[2,4-dichloro-β-(p-fluorophenylthio)carbonyloxy)phenethyl]imidazole;

1-[2,4-dichloro-β-(p-chlorobenzylthiolcarbonyloxy)phenethyl]imidazole;

1-[2,4-dichloro-β-(2,4-dichlorobenzylthiolcarbonyloxy)phenethyl]imidazole; and

1-[2,4-dichloro-β-(3,4-dichlorobenzylthiolcarbonyloxy)phenethyl]imidazole.

C. Similarly, by following the precedure of part A of this example but employing a 1-[β-hydroxyphenethyl]imidazole of Formula (III) having different $R^1$ substituents and also employing different S-hydrocarbyl chlorothioformates, other compounds such as the following may be prepared:

1-[4-t-butyl-β-(p-chlorobenzylthiolcarbonyloxy)phenethyl]imidazole;

1-[β-(2,3,4,5,6-pentachlorophenylthiolcarbonyloxy)phenethyl]imidazole;

and the like.

EXAMPLE 12

Cleavage of an Acid Salt to a Free Base

The oxalate salt of 1-[2,4-dichloro-β-(ethoxythiocarbonylthio)phenethyl]imidazole is prepared according the process set forth in Example 1, part A. Two g of this salt suspended in 100 ml of dichloromethane is shaken with excess dilute potassium carbonate solution until the salt is completely dissolved. The organic layer is then separated, washed twice with water, and dried over magnesium sulfate. The solvent is then evaporated to yield 1-[2,4-dichloro-β-(ethoxythiocarbonylthio)phenethyl]imidazole in base form as an oil.

In a similar manner, the acid addition salts of all compounds of Formula (I), particularly those representatives in Examples 1–11, can be converted to the corresponding compounds in base form.

EXAMPLE 13

Acid Salt Formation from a Free Base

Nitric acid (d=1.42) was added dropwise to a stirred solution of 500 mg. of 1-[2,4-dichloro-β-(ethoxythiocarbonylthio)phenethyl]imidazole in 30 ml anhydrous ether until precipitation was complete. The product was filtered off, washed with ether, air dried, and recrystallized from ethyl acetate/acetone to yield 1-[2,4-dichloro-β-(ethoxythiocarbonylthio)phenethyl]imidazole nitrate, mp 142.5°–143° C (foaming).

In similar manner, all compounds of Formula (I) in free base form can be converted to the acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, or p-toluenesulfonic acid.

EXAMPLE 14

The following example is included to illustrate the preparation of representative formulations which may be used to control fungi, protozoa or bacteria in humans and animals.

| A. Topical Formulation | |
| --- | --- |
| | grams |
| Active compound | 0.2 – 2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA(butylated hydroxy anisole) | 0.01 |
| Water    qs | 100 |

All of the above ingredients, except water, are combined and heated at 60° C. with stirring. A sufficient quantity of water at 60° C. is then added with vigorous stirring to provide 100 g. of the cream formulation which is then cooled to room temperature.

| B. I.V. Formulation | |
| --- | --- |
| Active compound | 0.5 g. |
| Propylene glycol | 20 g. |
| Polyethylene glycol 400 | 20 g. |
| Tween 80 | 1 g. |
| 0.9% Saline solution qs | 100 ml. |

The active compound is dissolved in propylene glycol, polyethylene glycol 400 and Tween 80. A sufficient quantity of 0.9% saline solution is then added with stirring to provide 100 ml. of the I.V. solution which is filtered through a 0.2 micron membrane filter and packaged under sterile conditions.

| C. Oral Formulation | |
| --- | --- |
| | parts by weight |
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg. of active compound) with an appropriate tabletting machine.

EXAMPLE 15

Preparation of 1-[β-(R-thio)phenethyl]imidazoles

A. Preparation of 1-[2,4-dichloro-β-(4-chlorobenzylthio)phenethyl]imidazole, nitrate 850 Milligrams of 1-[2,4-dichloro-β-(ethoxythiocarbonylthio)phenethyl]imidazole nitrate was added to a solution of sodium hydroxide (330 mg) in 30 ml. methanol under nitrogen and the mixture stirred at room temperature for about 30 minutes until no carbonate remained as indicated by thin layer chromatography. To the resulting solution 350 mg. of α,p-dichlorotoluene was added, and the mixture stirred for 30 minutes before removal of the solvent under reduced pressure. Ether and water were then added to the residue and the extract washed with water and dried over magnesium sulfate. Dropwise, addition of nitric acid (d = 1.42) to the ethereal solution precipitated the nitrate salt of 1-[2,4-dichloro-β-(4-chlorobenzylthio)phenethyl]imidazole, mp 130.5°–132° C when recrystallized from acetone.

B. By following a procedure similar to that set forth in part A of this example, but substituting n-heptyl bromide and α,2,4-trichlorotoluene for α,p-dichlorotoluene, the following respective compounds are prepared:

1-[2,4-dichloro-β-(n-heptylthio)phenethyl]imidazole oxalate. mp 106°–109° C and

1-[2,4-dichloro-β-(2,4-dichlorobenzylthio)phenethyl]imidazole nitrate, mp 133.5°–134.5° C.

C. By following a procedure similar to that set forth in parts A and B of this example but substituting other 1-[β-(R-oxythiocarbonylthio)phenethyl]imidazoles or 1-[β-(R-oxycarbonythio)phenethyl]imidazoles, 1-[β-(R-thiolcarbonylthio)phenethyl]imidazoles, or 1-[β-(R-thiolthiocarbonylthio)phenethyl]imidazoles for 1-[2,4-dichloro-β-(ethoxythiocarbonylthio)phenethyl]imidazole and other appropriate R² halides for α,p-dichlorotoluene, the corresponding 1-[R¹-β-(R-thio)phenethyl]imidazoles are obtained.

I claim as my invention:

1. A compound selected from those represented by the formula

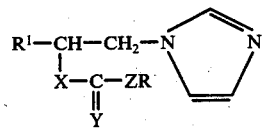

wherein
R is alkyl of 1 to 12 carbon atoms, phenylalkenyl, cycloalkyl, cycloalkyl lower alkyl, phenylalkyl, or phenyl, said phenyl, phenylalkyl, and phenylalkenyl each being independently optionally substituted with at least one substituent on the phenyl moiety selected from the group consisting of halo, lower alkyl, and trifluoromethyl;

R¹ is phenyl optionally substituted with at least one substituent chosen from the group consisting of halo, lower-alkyl and trifluoromethyl; and X, Y and Z are independently sulfur or oxygen and the antimicrobial acid addition salts thereof.

2. The compound of claim 1 wherein R¹ is chosen from the group consisting of 4-halophenyl, 2,4-dihalophenyl, 3,4-dihalophenyl and 2,4,6-trichlorophenyl and the antimicrobial addition salts thereof.

3. The compound of claim 1 wherein R is chosen from the group consisting of alkyl of up to 10 carbon atoms, 3-phenyl-2-propenyl optionally substituted on the 4 position of the phenyl ring with halo, phenyl optionally substituted with 1 or more halo or lower alkyl substituents, and benzyl optionally substituted on the phenyl ring with 1 or more halo or lower alkyl substituents and the antimicrobial acid addition salts thereof.

4. The compound of claim 3 wherein R¹ is 2,4-dichlorophenyl; R is alkyl of 1–7 carbon atoms, phenyl substituted with halo at 1 or 2 positions, benzyl substituted at the 4 position with a halo or at the 2,4- or 3,4- positions with chloro; X is S; and Y and Z are independently S or O and the antimicrobial acid addition salts thereof.

5. The compound of claim 4 wherein R is ethyl, 1-[2,4-dichloro-β-(ethoxythiocarbonylthio)phenethyl]imidazole and the antimicrobial acid addition salts thereof.

6. The compound of claim 4 wherein R is n-propyl, 1-[2,4-dichloro-β-(n-propoxythiocarbonylthio)phenethyl]imidazole and the antimicrobial acid addition salts thereof.

7. The compound of claim 4 wherein R is n-butyl, 1-[2,4-dichloro-β-(n-butoxythiocarbonylthio)phenethyl]imidazole and the antimicrobial acid addition salts thereof.

8. The compound of claim 4 wherein R is n-pentyl, 1-[2,4-dichloro-β-(n-pentyloxythiocarbonylthio)phenethyl]imidazole and the antimicrobial acid addition salts thereof.

9. The compound of claim 4 wherein R is p-chlorobenzyl, 1-[2,4-dichloro-β-(p-chlorobenzyloxythiocarbonylthio)phenethyl]imidazole and the antimicrobial acid addition salts thereof.

10. The compound of claim 4 wherein R is 2,4-dichlorobenzyl, 1-[2,4-dichloro-β-(2,4-dichlorobenzyloxythiocarbonylthio)phenethyl]imidazole and the antimicrobial acid addition salts thereof.

11. The compound of claim 4 wherein R is 3,4-dichlorobenzyl, 1-[2,4-dichloro-β-(3,4-dichlorobenzyloxythiocarbonylthio)phenethyl]imidazole and the antimicrobial acid addition salts thereof.

12. The compound of claim 4 wherein R is p-chlorophenyl, 1-[2,4-dichloro-β-(p-chlorophenoxythiocarbonylthio)phenethyl]imidazole and the antimicrobial acid addition salts thereof.

13. The compound of claim 4 wherein R is 2,4-dichlorophenyl, 1-[2,4-dichloro-β-(2,4-dichlorophenoxythiocarbonylthio)phenethyl]imidazole and the antimicrobial acid addition salts thereof.

14. The compound of claim 4 wherein R is 3,4-dichlorophenyl, 1-[2,4-dichloro-β-(3,4-dichlorophenoxythiocarbonylthio)phenethyl]imidazole and the antimicrobial acid addition salts thereof.

15. The compound of claim 4 wherein R is ethyl, 1-[2,4-dichloro-β-(ethylthiolcarbonylthio)phenyl]imidazole and the antimicrobial acid addition salts thereof.

16. The compound of claim 4 wherein R is n-propyl, 1-[2,4-dichloro-β-(n-propylthiolcarbonylthio)phenethyl]imidazole and the antimicrobial acid addition salts thereof.

17. The compound of claim 4 wherein R is n-butyl, 1-[2,4-dichloro-β-(n-butylthiolcarbonylthio)phenethyl]imidazole and the antimicrobial acid addition salts thereof.

18. The compound of claim 4 wherein R is n-pentyl, 1-[2,4-dichloro-β-(n-pentylthiolcarbonylthio)phenethyl]imidazole and the antimicrobial acid addition salts thereof.

19. The compound of claim 4 wherein R is phenyl, 1-[2,4-dichloro-β-(phenylthiolcarbonylthio)phenethyl]imidazole and the antimicrobial acid addition salts thereof.

20. The compound of claim 4 wherein R is p-fluorophenyl, 1-[2,4-dichloro-β-(p-fluorophenylthiolcarbonylthio)phenethyl]imidazole and the antimicrobial acid addition salts thereof.

21. The compound of claim 4 wherein R is p-chlorophenyl, 1-[2,4-dichloro-β-(p-chlorophenylthiolcarbonylthio)phenethyl]imidazole and the antimicrobial acid addition salts thereof.

22. The compound of claim 4 wherein R is 2,4-dichlorophenyl, 1-[2,4-dichloro-β-(2,4-dichlorophenylthiolcarbonylthio)phenethyl]imidazole and the antimicrobial acid addition salts thereof.

23. The compound of claim 4 wherein R is 3,4-dichlorophenyl, 1-[2,4-dichloro-β-(3,4-dichlorophenylthiolcarbonylthio)phenethyl]imidazole and the antimicrobial acid addition salts thereof.

24. The compound of claim 4 wherein R is p-chlorobenzyl, 1-[2,4-dichloro-β-(p-chlorobenzylthiolcarbonylthio)phenethyl]imidazole and the antimicrobial acid addition salts thereof.

25. The compound of claim 4 wherein R is p-chlorophenyl, 1-[2,4-dichloro-β-(p-chlorophenoxycarbonylthio)phenethyl]imidazole and the antimicrobial acid addition salts thereof.

26. The compound of claim 4 wherein R is 2,4-dichlorophenyl, 1-[2,4-dichloro-β-(2,4-dichlorophenoxycarbonylthio)phenethyl]imidazole and the antimicrobial acid addition salts thereof.

27. The compound of claim 4 wherein R is 3,4-dichlorophenyl, 1-[2,4-dichloro-β-(3,4-dichlorophenoxycarbonylthio)phenethyl]imidazole and the antimicrobial acid addition salts thereof.

28. The compound of claim 4 wherein R is p-chlorobenzyl, 1-[2,4-dichloro-β-(p-chlorobenzyloxycarbonylthio)phenethyl]imidazole and the antimicrobial acid addition salts thereof.

29. The compound of claim 4 wherein R is 2,4-dichlorobenzyl, 1-[2,4-dichloro-β-(2,4-dichlorobenzyloxycarbonylthio)phenethyl]imidazole and the antimicrobial acid addition salts thereof.

30. The compound of claim 4 wherein R is 3,4-dichlorobenzyl, 1-[2,4-dichloro-β-(3,4-dichlorobenzyloxycarbonylthio)phenethyl]imidazole and the antimicrobial acid addition salts thereof.

31. The compound of claim 4 wherein R is p-chlorophenyl, 1-[2,4-dichloro-β-(p-chlorophenylthiolcarbonyloxy)phenethyl]imidazole and the antimicrobial acid addition salts thereof.

32. The compound of claim 4 wherein R is p-chlorobenzyl, 1-[2,4-dichloro-β-(p-chlorobenzylthiolcarbonyloxy)phenethyl]imidazole and the antimicrobial acid addition salts thereof.

33. A composition useful for inhibiting the growth of fungi, bacteria or protozoa which comprises 0.1–95% by weight of at least one compound selected from those represented by the formula

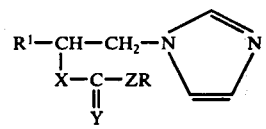

wherein
R is alkyl of 1 to 12 carbon atoms, phenylalkenyl, cycloalkyl, cycloalkyl lower alkyl, phenylalkyl, or phenyl, said phenyl, phenylalkyl, and phenylalkenyl each being independently optionally substituted with at least one substituent on the phenyl moiety selected from the group consisting of halo, lower alkyl, and trifluoromethyl;

$R^1$ is phenyl optionally substituted with at least one substituent chosen from the group consisting of halo, lower alkyl and trifluoromethyl; and X, Y and Z are independently sulfur or oxygen and the antimicrobial acid addition salts thereof in admixture with a suitable carrier.

34. The composition of claim 33 wherein $R^1$ is 2,4-dichlorophenyl.

35. The composition of claim 34 for pharmaceutical, topical application wherein the carrier is a pharmaceutically acceptable, non-toxic carrier and the compound of claim 1 is present in an amount ranging between 0.1 and 10.0 weight percent of the composition.

36. A method of inhibiting the growth of fungi, bacteria or protozoa which comprises applying to the host object containing, or subject to attack by, fungi, bacteria or protozoa, a fungicidally, bactericidally or protozoicidally effective amount of a compound represented by the formula $$R^1-CH-CH_2-N\diagdown N \diagup \quad\\ \phantom{R^1-}X-C-ZR \\ \phantom{R^1-XX}\|\\ \phantom{R^1-XX}Y$$

wherein
R is alkyl of 1 to 12 carbon atoms, phenylalkenyl, cycloalkyl, cycloalkyl lower alkyl, phenylalkyl, or phenyl, said phenyl, phenylalkyl, and phenylalkenyl each being independently optionally substituted with at least one substituent on the phenyl moiety selected from the group consisting of halo, lower alkyl, and trifluoromethyl;

$R^1$ is phenyl optionally substituted with at least one substituent chosen from the group consisting of halo, lower-alkyl and trifluoromethyl; and X, Y and Z are independently sulfur or oxygen and the antimicrobial acid addition salts thereof or a composition containing same as active ingredient.

37. The method of claim 36 wherein $R^1$ is 2,4-dichlorophenyl.

* * * * *